US009571143B2

(12) United States Patent
Richley

(10) Patent No.: US 9,571,143 B2
(45) Date of Patent: Feb. 14, 2017

(54) INTERFERENCE REJECTION IN ULTRA-WIDEBAND REAL TIME LOCATING SYSTEMS

(71) Applicant: ZIH Corp., Lincolnshire, IL (US)

(72) Inventor: Edward A. Richley, Germantown, MD (US)

(73) Assignee: ZIH Corp., Lincolnshire, IL (US)

( * ) Notice: Subject to any disclaimer, the term of this patent is extended or adjusted under 35 U.S.C. 154(b) by 0 days.

(21) Appl. No.: 13/942,244

(22) Filed: Jul. 15, 2013

(65) Prior Publication Data

US 2014/0364078 A1     Dec. 11, 2014

Related U.S. Application Data

(60) Provisional application No. 61/831,990, filed on Jun. 6, 2013.

(51) Int. Cl.
    *H04B 1/10*            (2006.01)
    *G06F 17/30*          (2006.01)
    (Continued)

(52) U.S. Cl.
    CPC ......... *H04B 1/1036* (2013.01); *A63B 24/0021* (2013.01); *A63B 24/0062* (2013.01);
    (Continued)

(58) Field of Classification Search
    CPC .......... H04B 1/00; H04B 1/10; H04B 1/1036; H04B 1/16; H04B 1/406; H04B 1/71; H04B 1/71637; H04B 1/7097; H03J 3/26; H03J 2200/14; G06K 7/10227; G06K 7/10297; G06K 7/10366; G06K 7/10306; G06K 9/00342; G06F 17/30876; H04L 67/12; A63B 24/0062; A63B 71/0622; A63B 71/0619; A63B 71/06; G08C 17/02; H04W 4/02
    (Continued)

(56) References Cited

U.S. PATENT DOCUMENTS

| 3,732,500 A | 5/1973 | Dishal et al. |
| 5,046,133 A | 9/1991 | Watanabe et al. |

(Continued)

FOREIGN PATENT DOCUMENTS

| EP | 1235077 A2 | 8/2002 |
| EP | 1241616 A2 | 9/2002 |

(Continued)

OTHER PUBLICATIONS

International Search Report and Written Opinion from International Application No. PCT/US2014/041062 dated Oct. 1, 2014.

(Continued)

*Primary Examiner* — Thanh Le
(74) *Attorney, Agent, or Firm* — Alston & Bird LLP

(57) ABSTRACT

Systems, methods, apparatuses, and computer readable media are disclosed for providing interference rejection in ultra-wideband real time locating systems. In one embodiment, an ultra-wideband (UWB) receiver is configured to: receive a composite signal, the composite signal comprising a UWB signal transmitted from within a monitored region and an interference signal transmitted from a source positioned outside the monitored region; filtering at least a first component of the composite signal representing the interference signal with a tunable notch filter to generate a filtered signal; determining an interference level in the filtered signal; and adjust the tunable notch filter to reduce the interference level. Corresponding systems, methods, and computer-readable storage medium are also provided.

17 Claims, 8 Drawing Sheets

(51) Int. Cl.

| | | |
|---|---|---|
| H04L 29/08 | (2006.01) | |
| A63B 24/00 | (2006.01) | |
| G06K 7/10 | (2006.01) | |
| G08C 17/02 | (2006.01) | |
| H04B 1/7097 | (2011.01) | |
| H04W 4/02 | (2009.01) | |
| A63B 71/06 | (2006.01) | |
| G06K 9/00 | (2006.01) | |
| G06F 19/00 | (2011.01) | |
| G06N 5/02 | (2006.01) | |
| H04L 12/26 | (2006.01) | |
| G06Q 50/20 | (2012.01) | |
| G09B 19/00 | (2006.01) | |
| H04B 1/7163 | (2011.01) | |
| H04B 1/719 | (2011.01) | |
| G06Q 50/22 | (2012.01) | |
| G06K 17/00 | (2006.01) | |
| G06Q 90/00 | (2006.01) | |

(52) U.S. Cl.
CPC .......... *A63B 71/06* (2013.01); *A63B 71/0619* (2013.01); *A63B 71/0622* (2013.01); *G06F 17/3087* (2013.01); *G06F 17/30864* (2013.01); *G06F 17/30876* (2013.01); *G06F 19/3437* (2013.01); *G06K 7/10227* (2013.01); *G06K 7/10297* (2013.01); *G06K 7/10306* (2013.01); *G06K 7/10366* (2013.01); *G06K 9/00342* (2013.01); *G06N 5/02* (2013.01); *G06Q 50/20* (2013.01); *G06Q 50/22* (2013.01); *G08C 17/02* (2013.01); *G09B 19/0038* (2013.01); *H04B 1/7097* (2013.01); *H04B 1/719* (2013.01); *H04B 1/71635* (2013.01); *H04B 1/71637* (2013.01); *H04L 43/04* (2013.01); *H04L 67/12* (2013.01); *H04W 4/02* (2013.01); *A63B 24/00* (2013.01); *A63B 2024/0025* (2013.01); *A63B 2220/836* (2013.01); *A63B 2225/50* (2013.01); *A63B 2225/54* (2013.01); *G06K 2017/0045* (2013.01); *G06Q 90/00* (2013.01)

(58) Field of Classification Search
USPC ............ 455/234.1, 254, 255, 259, 260, 266, 296, 455/307, 334, 339
See application file for complete search history.

(56) References Cited

U.S. PATENT DOCUMENTS

| | | |
|---|---|---|
| 5,119,104 A | 6/1992 | Heller |
| 5,469,409 A | 11/1995 | Anderson et al. |
| 5,513,854 A | 5/1996 | Daver |
| 5,645,077 A | 7/1997 | Foxlin |
| 5,699,244 A | 12/1997 | Clark et al. |
| 5,901,172 A | 5/1999 | Fontana et al. |
| 5,920,287 A | 7/1999 | Belcher et al. |
| 5,930,741 A | 7/1999 | Kramer |
| 5,995,046 A | 11/1999 | Belcher et al. |
| 6,028,626 A | 2/2000 | Aviv |
| 6,121,926 A | 9/2000 | Belcher et al. |
| 6,176,837 B1 | 1/2001 | Foxlin |
| 6,204,813 B1 | 3/2001 | Wadell et al. |
| 6,366,242 B1 | 4/2002 | Boyd et al. |
| 6,380,894 B1 | 4/2002 | Boyd et al. |
| 6,593,885 B2 | 7/2003 | Wisherd et al. |
| 6,655,582 B2 | 12/2003 | Wohl et al. |
| 6,710,713 B1 | 3/2004 | Russo |
| 6,812,884 B2 | 11/2004 | Richley et al. |
| 6,836,744 B1 | 12/2004 | Asphahani et al. |
| 6,882,315 B2 | 4/2005 | Richley et al. |
| 7,009,638 B2 | 3/2006 | Gruber et al. |
| 7,190,271 B2 | 3/2007 | Boyd et al. |
| 7,263,133 B1 | 8/2007 | Miao |
| 7,667,604 B2 | 2/2010 | Ebert et al. |
| 7,710,322 B1 | 5/2010 | Ameti et al. |
| 7,755,541 B2 | 7/2010 | Wisherd et al. |
| 7,899,006 B2 | 3/2011 | Boyd |
| 8,009,727 B2 | 8/2011 | Hui et al. |
| 8,023,917 B2 * | 9/2011 | Popescu ........................ 455/296 |
| 8,077,981 B2 | 12/2011 | Elangovan et al. |
| 8,269,835 B2 | 9/2012 | Grigsby |
| 8,279,051 B2 | 10/2012 | Khan |
| 8,568,278 B2 | 10/2013 | Riley et al. |
| 8,665,152 B1 | 3/2014 | Kling et al. |
| 8,696,458 B2 | 4/2014 | Foxlin et al. |
| 8,705,671 B2 | 4/2014 | Ameti et al. |
| 8,775,916 B2 | 7/2014 | Pulsipher et al. |
| 8,780,204 B2 | 7/2014 | DeAngelis et al. |
| 8,795,045 B2 | 8/2014 | Sorrells et al. |
| 8,842,002 B2 | 9/2014 | Rado |
| 8,989,880 B2 | 3/2015 | Wohl et al. |
| 9,081,076 B2 | 7/2015 | DeAngelis et al. |
| 9,381,645 B1 | 7/2016 | Yarlagadda et al. |
| 2001/0010541 A1 | 8/2001 | Fernandez et al. |
| 2001/0030625 A1 | 10/2001 | Doles et al. |
| 2002/0004398 A1 | 1/2002 | Ogino et al. |
| 2002/0041284 A1 | 4/2002 | Konishi et al. |
| 2002/0114493 A1 | 8/2002 | McNitt et al. |
| 2002/0130835 A1 | 9/2002 | Brosnan |
| 2002/0135479 A1 | 9/2002 | Belcher et al. |
| 2003/0090387 A1 | 5/2003 | Lestienne et al. |
| 2003/0095186 A1 | 5/2003 | Aman et al. |
| 2003/0128100 A1 | 7/2003 | Burkhardt et al. |
| 2003/0163287 A1 | 8/2003 | Vock et al. |
| 2003/0227453 A1 | 12/2003 | Beier et al. |
| 2004/0022227 A1 | 2/2004 | Lynch et al. |
| 2004/0062216 A1 * | 4/2004 | Nicholls ................... H04B 1/71 370/320 |
| 2004/0108954 A1 | 6/2004 | Richley et al. |
| 2004/0178960 A1 | 9/2004 | Sun |
| 2004/0249969 A1 | 12/2004 | Price |
| 2004/0260470 A1 | 12/2004 | Rast |
| 2004/0260828 A1 | 12/2004 | Price |
| 2005/0026563 A1 | 2/2005 | Leeper et al. |
| 2005/0031043 A1 | 2/2005 | Paquelet |
| 2005/0059998 A1 | 3/2005 | Norte et al. |
| 2005/0075079 A1 | 4/2005 | Jei et al. |
| 2005/0093976 A1 | 5/2005 | Valleriano |
| 2005/0148281 A1 | 7/2005 | Sanchez-Castro et al. |
| 2005/0207617 A1 | 9/2005 | Sarnoff |
| 2006/0067324 A1 | 3/2006 | Kim |
| 2006/0139167 A1 | 6/2006 | Davie et al. |
| 2006/0164213 A1 | 7/2006 | Burghard et al. |
| 2006/0252476 A1 | 11/2006 | Bahou |
| 2006/0271912 A1 | 11/2006 | Mickle et al. |
| 2006/0281061 A1 | 12/2006 | Hightower et al. |
| 2007/0091292 A1 | 4/2007 | Cho et al. |
| 2007/0176749 A1 | 8/2007 | Boyd et al. |
| 2007/0296723 A1 | 12/2007 | Williams |
| 2008/0065684 A1 | 3/2008 | Zilberman |
| 2008/0106381 A1 | 5/2008 | Adamec et al. |
| 2008/0113787 A1 | 5/2008 | Alderucci |
| 2008/0129825 A1 | 6/2008 | DeAngelis et al. |
| 2008/0186231 A1 | 8/2008 | Aljadeff et al. |
| 2008/0204248 A1 | 8/2008 | Winget et al. |
| 2008/0262885 A1 | 10/2008 | Jain et al. |
| 2008/0266131 A1 | 10/2008 | Richardson et al. |
| 2008/0269016 A1 | 10/2008 | Ungari et al. |
| 2008/0281443 A1 | 11/2008 | Rodgers |
| 2008/0285805 A1 | 11/2008 | Luinge et al. |
| 2009/0048044 A1 | 2/2009 | Oleson et al. |
| 2009/0141736 A1 | 6/2009 | Becker |
| 2009/0231198 A1 | 9/2009 | Walsh et al. |
| 2010/0026809 A1 | 2/2010 | Curry |
| 2010/0045508 A1 | 2/2010 | Ekbal et al. |
| 2010/0054304 A1 | 3/2010 | Barnes et al. |
| 2010/0060452 A1 | 3/2010 | Schuster et al. |
| 2010/0150117 A1 | 6/2010 | Aweya et al. |
| 2010/0228314 A1 | 9/2010 | Goetz |

(56) References Cited

U.S. PATENT DOCUMENTS

| | | |
|---|---|---|
| 2010/0250305 A1 | 9/2010 | Lee et al. |
| 2010/0278386 A1 | 11/2010 | Hoeflinger |
| 2010/0283630 A1 | 11/2010 | Alonso |
| 2010/0328073 A1 | 12/2010 | Nikitin et al. |
| 2011/0002223 A1 | 1/2011 | Gross |
| 2011/0025847 A1 | 2/2011 | Park et al. |
| 2011/0054782 A1 | 3/2011 | Kaahui et al. |
| 2011/0063114 A1 | 3/2011 | Ikoyan |
| 2011/0064023 A1 | 3/2011 | Yamamoto et al. |
| 2011/0134240 A1 | 6/2011 | Anderson et al. |
| 2011/0140970 A1 | 6/2011 | Fukagawa et al. |
| 2011/0169959 A1 | 7/2011 | DeAngelis et al. |
| 2011/0188513 A1 | 8/2011 | Christoffersson et al. |
| 2011/0195701 A1 | 8/2011 | Cook et al. |
| 2011/0261195 A1 | 10/2011 | Martin et al. |
| 2011/0300905 A1 | 12/2011 | Levi |
| 2011/0320322 A1 | 12/2011 | Roslak et al. |
| 2012/0014278 A1 | 1/2012 | Ameti et al. |
| 2012/0015665 A1 | 1/2012 | Farley et al. |
| 2012/0024516 A1 | 2/2012 | Bhadurt et al. |
| 2012/0042326 A1 | 2/2012 | Jain et al. |
| 2012/0057634 A1 | 3/2012 | Shi et al. |
| 2012/0057640 A1 | 3/2012 | Shi et al. |
| 2012/0081531 A1 | 4/2012 | DeAngelis et al. |
| 2012/0126973 A1 | 5/2012 | DeAngelis et al. |
| 2012/0139708 A1 | 6/2012 | Paradiso et al. |
| 2012/0184878 A1 | 7/2012 | Najafi et al. |
| 2012/0212505 A1 | 8/2012 | Burroughs et al. |
| 2012/0218301 A1 | 8/2012 | Miller |
| 2012/0225676 A1 | 9/2012 | Boyd et al. |
| 2012/0231739 A1 | 9/2012 | Chen et al. |
| 2012/0246795 A1 | 10/2012 | Scheffler et al. |
| 2012/0256745 A1 | 10/2012 | Plett et al. |
| 2012/0268239 A1 | 10/2012 | Ljung et al. |
| 2013/0003860 A1 | 1/2013 | Sasai et al. |
| 2013/0021142 A1 | 1/2013 | Matsui et al. |
| 2013/0021206 A1 | 1/2013 | Hach et al. |
| 2013/0040574 A1 | 2/2013 | Hillyard |
| 2013/0041590 A1 | 2/2013 | Burich et al. |
| 2013/0066448 A1 | 3/2013 | Alonso |
| 2013/0076645 A1 | 3/2013 | Anantha et al. |
| 2013/0096704 A1 | 4/2013 | Case |
| 2013/0115904 A1* | 5/2013 | Kapoor et al. ............ 455/307 |
| 2013/0138386 A1 | 5/2013 | Jain et al. |
| 2013/0142384 A1 | 6/2013 | Ofek |
| 2013/0257598 A1 | 10/2013 | Kawaguchi et al. |
| 2013/0339156 A1 | 12/2013 | Sanjay et al. |
| 2014/0055588 A1 | 2/2014 | Bangera et al. |
| 2014/0145828 A1 | 5/2014 | Bassan-Eskenazi |
| 2014/0156036 A1 | 6/2014 | Huang |
| 2014/0170607 A1 | 6/2014 | Hsiao et al. |
| 2014/0221137 A1 | 8/2014 | Krysiak et al. |
| 2014/0320660 A1 | 10/2014 | DeAngelis et al. |
| 2014/0361875 A1 | 12/2014 | O'Hagan et al. |
| 2014/0361906 A1 | 12/2014 | Hughes et al. |
| 2014/0364141 A1 | 12/2014 | O'Hagan et al. |
| 2014/0365415 A1 | 12/2014 | Stelfox et al. |
| 2015/0002272 A1 | 1/2015 | Alonso et al. |
| 2015/0057981 A1 | 2/2015 | Gross |
| 2015/0085111 A1 | 3/2015 | Lavery |
| 2015/0097653 A1 | 4/2015 | Gibbs et al. |
| 2015/0355311 A1 | 12/2015 | O'Hagan et al. |
| 2015/0358852 A1 | 12/2015 | Richley et al. |
| 2015/0360133 A1 | 12/2015 | MacCallum et al. |
| 2015/0375041 A1 | 12/2015 | Richley et al. |
| 2015/0375083 A1 | 12/2015 | Stelfox et al. |
| 2015/0378002 A1 | 12/2015 | Hughes et al. |
| 2015/0379387 A1 | 12/2015 | Richley |
| 2016/0097837 A1 | 4/2016 | Richley et al. |

FOREIGN PATENT DOCUMENTS

| | | |
|---|---|---|
| EP | 1253438 A2 | 10/2002 |
| EP | 1503513 A1 | 2/2005 |
| EP | 2474939 A1 | 11/2012 |
| WO | WO-9805977 A1 | 2/1998 |
| WO | WO 99/61936 A1 | 12/1999 |
| WO | WO 0108417 | 2/2001 |
| WO | WO 2006/022548 | 3/2006 |
| WO | WO-2010/083943 A1 | 7/2010 |
| WO | WO 2015/051813 A1 | 4/2014 |
| WO | WO 2014197600 | 12/2014 |

OTHER PUBLICATIONS

International Search Report and Written Opinion from International Application No. PCT/US2014/040947 dated Oct. 9, 2014.

Fontana, R.J., Richley, E., Barney, J., "Commercialization of an Ultra Wideband Precision Asset Location System," *2003 IEEE Conference on Ultra Wideband Systems and Technologies*, Nov. 16-19, 2003.

Gueziec, A., "Tracking Pitches for Broadcast Television," *Computer*, Aug. 7, 2002.

CattleLog Pro, *eMerge Interactive, Inc.*, Sebastian, FL, 2004.

Marchant, J., Secure Animal Identification and Source Verification, *JM Communications*, UK, 2002.

"A Guide to Using NLIS Approved Ear Tags and Rumen Boluses," National Livestock Identification Scheme, *Meat &Livestock Australia Limited*, North Sydney, Australia, May 2003.

King, L., "NAIS Cattle ID Pilot Projects Not Needed, Since Proven Advanced Technology Already Exists," *ScoringSystem, Inc.*, Sarasota, FL, Dec. 27, 2005. (www.prweb.com/release/2005/12prweb325888.htm).

"RFID in the Australian Meat and Livestock Industry," Allflex Australia Pty Ltd,Capalaba, QLD (AU), *Data Capture Suppliers Guide*, 2003-2004.

International Search Report and Written Opinion from International Application No. PCT/US2014/040881 dated Nov. 4, 2014.

International Search Report and Written Opinion from International Application No. PCT/US2014/040940 dated Dec. 17, 2014.

Complaint Before the United States District Court of Massachusetts, Civil Action No. 1:15-cv-12297, *Lynx System Developers, Inc. et al. v. Zebra Enterprise Solutions Corporation et al.*, filed Jun. 10, 2015.

International Search Report and Written Opinion for International Application No. PCT/IB2015/054099 dated Dec. 9, 2015.

Invitation to Pay Additional Fees/Partial International Search Report for PCT/IB2015/054099 dated Oct. 6, 2015.

Swedberg, C., "N.J. Company Seeks to Market Passive Sensor RFID Tags", RFID Journal, Jun. 14, 2011, <http://www.rfidjournal.com/articles/pdf?8527>.

U.S. Appl. No. 14/296,703, filed Jun. 5, 2014; In re: Alonso et al., entitle *Method and Apparatus for Associating Radio Frequency Identification Tags with Participants*.

U.S. Appl. No. 61/895,548, filed Oct. 25, 2013, In re: Alonso et al., entitled "*Method, Apparatus, and Computer Program Product for Collecting Sporting Event Data Based on Real Time Data for Proximity and Movement of Objects*"

International Search Report and Written Opinion for International Application No. PCT/IB2015/059264 dated Feb. 10, 2016.

Jinyun Zhang et al., "UWB Systems for Wireless Sensor Networks", Proceedings of the IEEE, IEEE. New York, US, vol. 97, No. 2, Feb. 1, 2009, pp. 313-331.

International Search Report and Written Opinion for International Application No. PCT/US2015/034267 dated Sep. 25, 2015.

International Search Report and Written Opinion for International Application No. PCT/IB2015/054103 dated Aug. 14, 2015.

Cheong, P. et al., "Synchronization, TOA and Position Estimation for Low-Complexity LDR UWB Devices", Ultra-Wideband, 2005 IEEE International Conference on Zurich, Switzerland Sep. 5-8, 2005, Piscataway, NJ, USA, IEEE, Sep. 5, 2005, pp. 480-484.

International Search Report and Written Opinion for International Application No. PCT/IB2015/054213 dated Aug. 6, 2015.

Wang, Y. et al., "An Algorithmic and Systematic Approach from Improving Robustness of TOA-Based Localization", 2013 IEEE 10th International Conference on High Performance Computing and Communications & 2013 IEEE, Nov. 13, 2013, pp. 2066-2073.

(56) References Cited

OTHER PUBLICATIONS

Guvenc, I. et al., "A Survey on TOA Based Wireless Localization and NLOA Mitigation Techniques", IEEE Communications Surveys, IEEE, New York, NY, US, vol. 11, No. 3, Oct. 1, 2009, pp. 107-124.

International Search Report and Written Opinion for International Application PCT/IB2015/054102 dated Nov. 4, 2015.

"Seattleite wins top prize in Microsoft's Super Bowl tech Contest", San Francisco AP, Komonews.com, Feb. 6, 2016. <http://komonews.com/news/local/seattleite-wins-top-prize-in-microsofts-super-bowl-tech-contest>.

Bahle et al., "I See You: How to Improve Wearable Activity Recognition by Leveraging Information from Environmental Cameras," Pervasive Computing and Communications Workshops, IEEE International Conference, (Mar. 18- 22, 2013).

Teixeira et al., "Tasking Networked CCTV Cameras and Mobile Phones to Identify and Localize Multiple People," Ubicomp '10 Proceedings of the 12th ACM International Conference on Ubiquitous Computing, pp. 213-222 (Sep. 26-29, 2010).

Complaint before the United States District Court of Massachusetts, Civil Action No. 1:15-cv-12297, *Lynx System Developers, Inc. et al.* V. *Zebra Enterprise Solutions Corporation et al.*, filed Mar. 23, 2016.

International Search Report for International Application No. PCT/US2014/053647 dated Dec. 19, 2014.

International Search Report and Written Opinion for International Application No. PCT/US2016/035614 dated Sep. 15, 2016.

Defendant's Answer to Compaint before the United States District Court of Massachusetts, Civil Action No. 1:15-cv-12297, *Lynx System Developers, Inc. et al.* V. *Zebra Enterprise Solutions Corporation et al.*, filed Apr. 6, 2016.

European Search Report for European Patent Application No. 14806811.7 dated Dec. 9, 2016.

\* cited by examiner

INTERFERENCE REJECTION IN ULTRA-WIDEBAND REAL TIME LOCATING SYSTEMS

CROSS-REFERENCE TO RELATED APPLICATION

This application claims priority from and the benefit of the filing date of U.S. Provisional Patent Application No. 61/831,990 filed Jun. 6, 2013, the contents of which is incorporated by reference in its entirety herein.

FIELD

Embodiments discussed herein are related to radio frequency locating and, more particularly, to systems, methods, apparatuses, computer readable media and other means for providing interference rejection.

BACKGROUND

A number of deficiencies and problems associated with UWB Real Time Locating Systems particularly related to interference are identified herein. Through applied effort, ingenuity, and innovation, exemplary solutions to many of these identified problems are embodied by the present invention, which is described in detail below.

BRIEF SUMMARY

Systems, methods, apparatuses, and computer readable media are disclosed for providing interference rejection in Ultra-Wideband Real Time Locating Systems.

Embodiments of the present invention may provide for interference rejection in Ultra-Wideband (UWB) Real Time Locating Systems (RTLS). Embodiments may provide for mitigation of the interference caused by other nearby telecommunications systems or equipment by taking advantage of aspects of the ultra-wideband signal relative to a typical interference signal.

In one embodiment, a UWB receiver is provided comprising a first antenna configured to receive a first signal, the first signal comprising a UWB signal and a first component of an interference signal; and a second antenna configured to receive a second signal, the second signal comprising at least a second component of the interference signal. The UWB receiver further comprises a combiner configured to receive the first signal from the first antenna; receive the second signal from the second antenna; and combine the first signal and the second signal to generate an output signal providing cancellation of at least part of the first component of the inference signal based at least in part on the second component of the interference signal.

In some embodiments, the UWB receiver may further comprise a controller; a detector; a variable attenuator; and a variable phase shifter. The detector may be configured to receive the output signal of the combiner and indicate an interference level in the output signal. The controller may be configured to monitor the interference level at the detector and adjust at least one of the variable attenuator and the variable phase shifter in an instance in which the monitored interference level is above a threshold level. The variable attenuator and the variable phase shifter may be configured to modify the second signal received from the second antenna and provide the modified second signal to the combiner.

In some embodiments, the UWB receiver may be configured such that the first antenna may be positioned in a first direction to receive signals transmitted from a monitored region and the second antenna may be positioned in a second direction, different from the first direction, to receive signals transmitted from outside the monitored region. In some embodiments, an interference signal may be generated by one or more communications systems positioned outside of a monitored region.

In another embodiment, a UWB receiver is provided comprising an antenna configured to receive a composite signal, the composite signal comprising a UWB signal and an interference signal. The UWB receiver further comprises a tunable notch filter configured to attenuate a part of the composite signal representing the interference signal thereby generating a filtered signal. The UWB receiver further comprises a detector configured to receive the filtered signal from the tunable notch filter and indicate an interference level in the filtered signal. The UWB receiver further comprises a controller and a voltage controlled oscillator; the controller configured to monitor the interference level at the detector and adjust the frequency of the voltage controlled oscillator in an instance in which the monitored interference level is above a threshold level; and the voltage controlled oscillator configured to tune the tunable notch filter.

In some embodiments, the tunable notch filter may comprise a first mixer, a notch filter, a second mixer, a splitter, and a voltage controlled oscillator. The first mixer may be configured to perform a downconversion of the received composite signal. The notch filter may be configured to attenuate part of the composite signal representing the interference signal. The second mixer may be configured to upconvert a notched signal back to the desired band. The splitter may be configured to provide the output of the voltage controlled oscillator to the first mixer and the second mixer. The voltage controlled oscillator may be configured to provide a frequency to the splitter that adjusts interference filtering of the tunable notch filter.

In still another embodiment, a method for providing interference rejection may include receiving a composite signal, the composite signal comprising a UWB signal transmitted from within a monitored region and an interference signal transmitted from a source positioned outside the monitored region. The method further includes filtering some amount of the composite signal with a tunable notch filter, to provide rejection of at least part of the interference signal, to generate a filtered signal. The method further includes monitoring the filtered signal, determining an amount of interference in the filtered signal, and adjusting the tunable notch filter to increase the interference filtering in an instance in which the amount of interference is above a threshold level. The method further includes processing the filtered signal.

In some embodiments, the signal may be received by a UWB receiver.

In another embodiment, a method for providing interference rejection includes receiving a first signal at a first antenna, wherein the first signal is a composite signal comprising a UWB signal and a first component of an interference signal; and receiving a second signal at a second antenna, wherein the second signal comprises at least a second component of the interference signal. The method further includes combining the first signal and the second signal to reduce the effect of the interference signal, and processing the combined signal.

In some embodiments, the combined signal may be provided by a combiner. In some embodiments, the method may further include monitoring the filtered signal; determining an amount of interference in the filtered signal; and if the amount of interference is above a threshold level, adjusting the second signal inputs to the combiner to increase filtering of the interference signal.

In some embodiments, the interference signal may be generated by one or more communications systems positioned outside of a monitored region. In some embodiments, the first antenna may be positioned in a first direction to receive signals transmitted from a monitored region and the second antenna may be positioned in a second direction, different from the first direction, to receive signals transmitted from outside the monitored region.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Overview

Figure 1A:
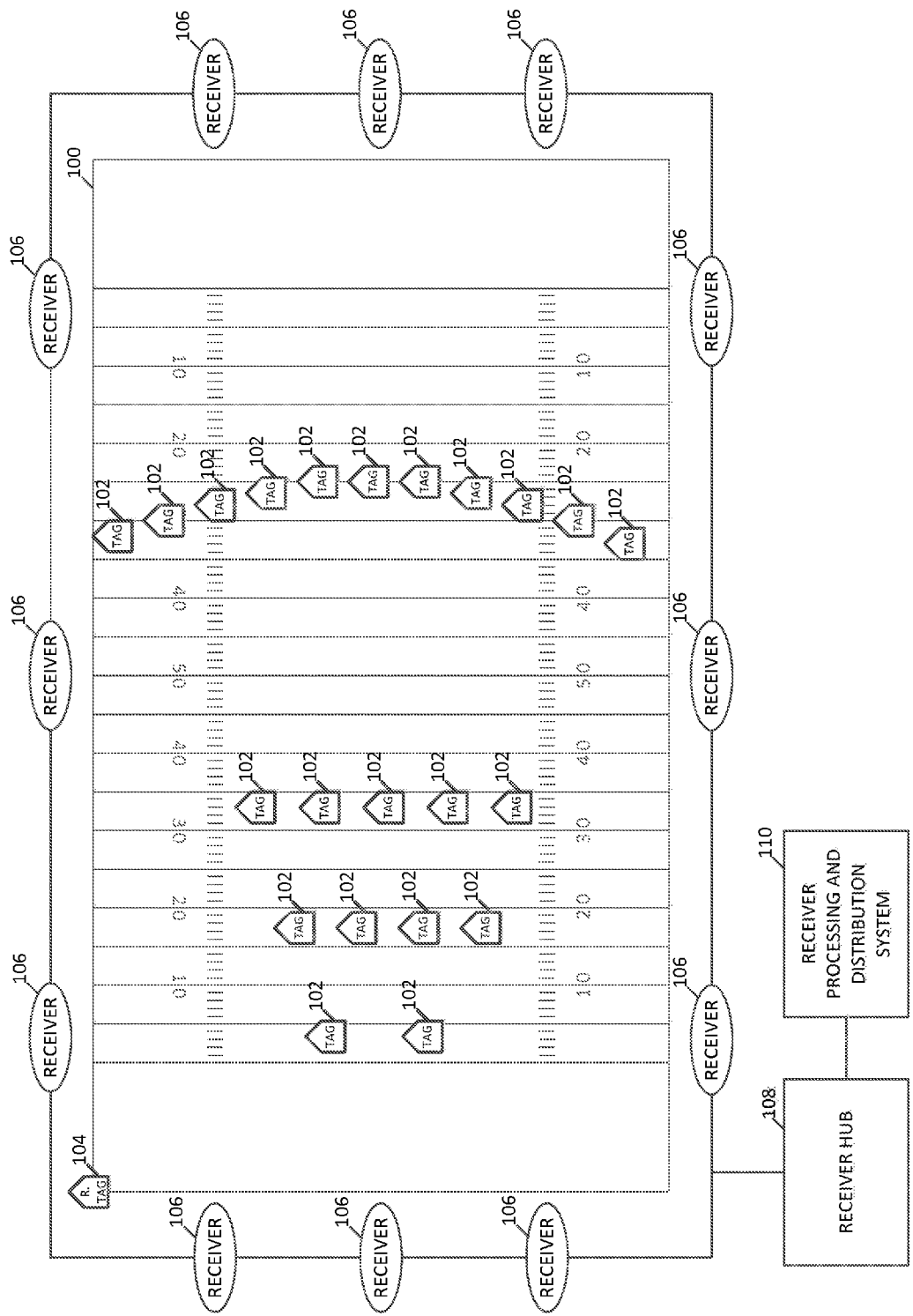
FIG. 1A illustrates an exemplary environment using a radio frequency locating system for providing performance analytics in accordance with some embodiments of the present invention.

Ultra-Wideband ("UWB") radio technology may be used for real-time tracking of objects. In some example UWB systems, autonomous tags may transmit short packets of digital information utilizing short pulses with very large bandwidth (typically 500 MHz) and, hence, may enjoy fine time resolution (~1 ns), often in the microwave region (typically the C-band). When deployed in an outdoor environment, such as illustrated in FIG. 1A, these UWB systems, owing to their large bandwidth requirement and strict regulatory constraints on transmitted power, are often very susceptible to interference from transmissions of licensed operators of various types of telecommunications equipment. In some examples, these licensed operators typically have legal priority over the unlicensed (FCC Part 15) operators of a UWB Real Time Locating System ("RTLS"). As a result, deployments in areas near point-to-point telecommunications links or satellite uplinks, for example, are subject to degraded performance due to the high probability that transmissions from these licensed services will occupy some portion of the wide bandwidth used by the UWB RTLS system.

Embodiments of the present invention are directed to methods, systems, apparatuses, and computer readable storage media for providing interference rejection in Ultra-Wideband Real Time Locating Systems. Embodiments of the present invention may provide for mitigation of the interference caused by transmissions from other nearby licensed telecommunications systems or equipment by taking advantage of aspects of the UWB signal relative to a typical interference signal. For example, some embodiments described herein exploit the short bursts of approximately 2 ns in duration of the UWB signal in contrast to the interference signals that are generally of a relatively narrowband nature, occupying a smaller bandwidth than the UWB system, and have a more continuous envelope. Additionally, because interference sources are often located outside the desired area of coverage of the UWB RTLS system, but are of such amplitude that a stray leakage path has sufficient strength to degrade performance of the UWB RTLS system, the difference in location may also be used in some embodiments to provide for mitigation of the interference signal.

The embodiments described herein provide potential solutions for the mitigation of inference signals including processing a received signal through tunable notch filters to mitigate the interference signal and combing two received signals in such a way as to reduce the effects of the interference signal.

Example RF Locating System Architecture

FIG. 1A illustrates an exemplary radio frequency ("RF") locating system useful for determining the position of an object (e.g., a participant, a football player on a football field, etc.) by determining tag 102 (e.g., an ultra-wideband (UWB) location tag) location information at each receiver 106 (e.g., UWB reader, etc.); a timing reference clock to synchronize the frequency of counters within each receiver 106; and, in some examples, a reference tag 104, preferably a UWB transmitter, positioned at known coordinates to enable phase offset between counters to be determined. The systems described herein may be referred to as either "multilateration" or "geolocation" systems; terms which refer to the process of locating a signal source by solving the mathematical intersection of multiple hyperbolae determined by the difference of arrival times between signals received at multiple receivers. Embodiments of the present invention may provide benefits to such a RF locating system (e.g., a UWB RTLS) by providing interference rejection for the system and, thus, providing improved UWB signal reception.

In some examples, the system comprising at least the tags 102 and the receivers 106 is configured to provide two dimensional and/or three dimensional precision localization (e.g., subfoot resolutions), even in the presence of multipath interference, due in part to the use of short nanosecond duration pulses whose time-of-flight can be accurately determined using detection circuitry, such as in the receivers 106, which can trigger on the leading edge of a received waveform. In some examples, this short pulse characteristic allows necessary data to be conveyed by the system at a higher peak power, but lower overall power levels, than a wireless system configured for high data rate communications, yet still operate within local regulatory requirements which may limit overall power levels.

In some examples, the tags 102 may operate with an instantaneous −3 dB bandwidth of approximately 400 MHz and an average transmission rate below a 187.5 kHz regulatory cutoff. In such examples, the predicted maximum range of the system, operating with a center frequency of 6.55 GHz, is roughly 311 meters. Such a configuration advantageously satisfies constraints applied by regulatory bodies related to peak and average power densities (e.g., effective isotropic radiated power density), while still optimizing system performance related to range and interference. In further examples, tag transmissions with a −3 dB bandwidth of approximately 400 MHz yields, in some examples, an instantaneous pulsewidth of roughly 2.5 nanoseconds that enables a location resolution to better than 30 centimeters.

Referring again to FIG. 1, the object to be located has an attached tag 102, preferably a tag having a UWB transmitter, that transmits a burst (e.g., 72 pulses at a 1 Mb/s burst rate), and optionally, a burst comprising an information packet utilizing on-off keying (OOK) that may include, but is not limited to, ID information, a sequential burst count or other desired information for object or personnel identification, inventory control, etc. In some examples, the sequential burst count (e.g., a packet sequence number) from each tag 102 may be advantageously provided in order to permit, at a receiver hub 108, correlation of TOA measurement data from various receivers 106.

In some examples, the tag 102 may employ UWB waveforms (e.g., low data rate waveforms) to achieve extremely fine resolution because of their extremely short pulse (i.e., sub-nanosecond to nanosecond, such as a 2 ns (1 ns up and 1 ns down)) durations. As such, the information packet may be of a short length (e.g., 72-112 bits in some example embodiments), that advantageously enables a higher throughput and higher transmission rates. In some examples, higher throughput and/or higher transmission rates may result in larger datasets for filtering to achieve a more accurate location estimate. In some examples, rates of up to approximately 2600 updates per second can be accommodated without exceeding regulatory requirements. Alternatively or additionally, in some examples, the length of the information packets, in conjunction with other system functionality, may also result in a longer battery life (e.g., a 3.0 v 300 mA-hr lithium cell battery may result in a tag battery life in excess of 7 years).

In some examples, one or more other tags, such as a reference tag 104, may be positioned within and/or about a monitored region, such as monitored region 100 illustrated herein as a football field. In some examples, the reference tag 104 may be configured to transmit a signal that is used to measure the relative phase (e.g., the count of free-running counters) of non-resettable counters within the receivers 106.

One or more (preferably four or more) receivers 106 are also positioned at predetermined coordinates within and/or around the monitored region 100. In some examples, the receivers 106 may be connected in a "daisy chain" fashion to advantageously allow for a large number of receivers 106 to be interconnected over a significant monitored region in order to reduce and simplify cabling, reduce latency, provide power, and/or the like. Each of the receivers 106 includes a receiver for receiving transmissions, such as UWB transmissions, and preferably, a packet decoding circuit that extracts a time of arrival (TOA) timing pulse train, transmitter ID, packet number, and/or other information that may have been encoded in the tag transmission signal (e.g., material description, personnel information, etc.) and is configured to sense signals transmitted by the tags 102 and one or more reference tags 104 (if present).

Each receiver 106 includes a time measuring circuit that measures time differences of arrival (TDOA) of tag bursts. The time measuring circuit is phase-locked (e.g., phase differences do not change and therefore respective frequencies are identical) with a common digital reference clock signal distributed via cable connection from a receiver hub 108 having a central timing reference clock generator. The reference clock signal establishes a common timing reference for the receivers 106. Thus, multiple time measuring circuits of the respective receivers 106 are synchronized in frequency, but not necessarily in phase. While there typically may be a phase offset between any given pair of receivers in the receivers 106, the offset is readily determined through use of a reference tag 104. Alternatively or additionally, each receiver may be synchronized wirelessly via virtual synchronization without a dedicated physical timing channel.

In some example embodiments, the receivers 106 are configured to determine various attributes of the received signal. Since measurements are determined at each receiver 106, in a digital format, rather than analog, signals are transmittable to the receiver hub 108. Advantageously, because packet data and measurement results can be transferred at high speeds to a receiver memory, the receivers 106 can receive and process tag (and corresponding object) locating signals on a nearly continuous basis. As such, in some examples, the receiver memory allows for a high burst rate of tag events (i.e., information packets) to be captured.

Data cables or wireless transmissions may convey measurement data from the receivers 106 to the receiver hub 108 (e.g., the data cables may enable a transfer speed of 2 Mbps). In some examples, measurement data is transferred to the receiver hub at regular polling intervals.

As such, the receiver hub 108 determines or computes tag position (i.e., object position) by processing TDOA measurements relative to multiple data packets detected by the receivers 106. In some example embodiments, the receiver hub 108 may be configured to resolve the coordinates of a tag using nonlinear optimization techniques.

In some examples, the system described herein may be referred to as an "over-specified" or "over-determined" system. As such, the receiver hub 108 may then calculate one or more valid (i.e., most correct) positions based on a set of measurements and/or one or more incorrect (i.e., less correct) positions. For example, a position may be calculated that is impossible due the laws of physics (e.g., a tag on a football player that travels more than 100 yards in 1 second) or may be an outlier when compared to other positions. As such one or more algorithms or heuristics may be applied to minimize such error.

One such algorithm for error minimization, which may be referred to as a time error minimization algorithm, may be described as:

$$\varepsilon = \sum_{j=1}^{N}\sum_{k=j+1}^{N}\left\{(t_j - t_k) - \frac{1}{c}\left[[(x-x_j)^2 + (y-y_j)^2 + (z-z_j)^2]^{\frac{1}{2}} - [(x-x_k)^2 + (y-y_k)^2 + (z-z_k)^2]^{\frac{1}{2}}\right]\right\}^2$$

where N is the number of receivers, c is the speed of light, $x_{j,k}$, $y_{j,k}$ and $z_{j,k}$ are the coordinates of the receivers and $t_{j,k}$ are the arrival times received at each of the receivers. Note that only time differences may be evaluated at hub 108 in some example embodiments. The starting point for the minimization may be obtained by first doing an area search on a coarse grid of x, y and z over an area defined by the user and followed by a localized steepest descent search.

Another or second algorithm for error minimization, which may be referred to as a distance error minimization algorithm, may be defined by:

$$\varepsilon = \sum_{j=1}^{N}\left[[(x-x_j)^2 + (y-y_j)^2 + (z-z_j)^2]^{\frac{1}{2}} - c(t_j - t_0)\right]^2$$

where time and position differences are replaced by their non-differential values by incorporating an additional unknown dummy variable, $t_0$, which represents an absolute time epoch. The starting point for this algorithm is fixed at the geometric mean position of all active receivers. No initial area search is needed, and optimization proceeds through the use of a DavidonFletcher-Powell (DFP) quasi-Newton algorithm in some examples. In other examples, a steepest descent algorithm may be used.

In order to determine the coordinates of a tag (T), in some examples and for calibration purposes, a reference tag (e.g., reference tag 104) is positioned at a known coordinate position ($x_T$, $y_T$, $z_T$).

In further example embodiments, a number N of receivers $\{R_j: j=1, \ldots, N\}$ (e.g., receivers 106) are positioned at known coordinates ($x_{Rj}$, $y_{Rj}$, $z_{Rj}$), which are respectively located at distances, such as:

$$d_{Rj} = \sqrt{(x_{Rj}-x_T)^2 + (y_{Rj}-y_T)^2 + (z_{Rj}-z_T)^2}$$

from a reference tag.

Each receiver $R_j$ utilizes, for example, a synchronous clock signal derived from a common frequency time base, such as clock generator. Because the receivers are not synchronously reset, an unknown, but constant offset $O_j$ exits for each receiver's internal free running counter. The value of the offset $O_j$ is measured in terms of the number of fine resolution count increments (e.g., a number of nanoseconds for a one nanosecond resolution system).

The reference tag is used to calibrate the radio frequency locating system as follows:

The reference tag emits a signal burst at an unknown time $\tau_R$. Upon receiving the signal burst from the reference tag, a count $N_R$, as measured at receiver $R_j$ is given by:

$$N_{Rj} = \beta\tau_R + O_j + \beta d_{Rj}/c$$

where c is the speed of light and β is the number of fine resolution count increments per unit time (e.g., one per nanosecond). Similarly, each object tag $T_i$ of each object to be located transmits a signal at an unknown time $\tau_i$ to produce a count $$N_{ij} = \beta\tau_i + O_j + \beta d_{ij}/c$$

at receiver $R_j$ where $d_{ij}$ is the distance between the object tag $T_i$ and the receiver at receiver $R_j$. Note that $\tau_i$ is unknown, but has the same constant value for receivers of all receivers $R_j$. Based on the equalities expressed above for receivers $R_j$ and $R_k$ and given the reference tag information, differential offsets expressed as differential count values are determined as follows:

$$N_{Rj} - N_{Rk} = (O_j - O_k) + \beta\left(\frac{d_{Rj}}{c} - \frac{d_{Rk}}{c}\right)$$

or $$(O_j - O_k) = (N_{Rj} - N_{Rk}) - \beta\left(\frac{d_{Rj}}{c} - \frac{d_{Rk}}{c}\right) = \Delta_{jk}$$

$\Delta_{jk}$ is constant as long as $d_{Rj} - d_{Rk}$ remains constant, (which means the receivers and tag are fixed and there is no multipath situation) and β is the same for each receiver. Note that $\Delta_{jk}$ is a known quantity, since $N_{Rj}$, $N_{Rk}$, β, $d_{Rj}/c$, and $d_{Rk}/c$ are known. That is, the differential offsets between receivers $R_j$ and $R_k$ may be readily determined based on the reference tag transmissions. Thus, again from the above equations, for an object tag ($T_i$) transmission arriving at receivers $R_j$ and $R_k$:

$$N_{ij} - N_{ik} = (O_j - O_k) + \beta(d_{ij}/c - d_{ik}/c) = \Delta_{jk} + \beta(d_{ij}/c - d_{ik}/c)$$

or, $$d_{ij} - d_{ik} = (c/\beta)[N_{ij} - N_{ik} - \Delta_{jk}].$$

The process further includes determining a minimum error value $E_i$, for each object tag $T_i$. In one algorithm, this proceeds according to the functional relationship:

$$E_i = \min_{(x,y,z)}\sum_j\sum_{k>j}\left[\left(\frac{c}{\beta}\right)(N_{ij} - N_{ik} - \Delta_{jk}) - (dist(T_{x,y,z}, R_j) - dist(T_{x,y,z}, R_k))\right]^2$$

or $$E_i = \min_{(x,y,z)}\sum_j\sum_{k>j}\left[(d_{ij} - d_{ik}) - (dist(T_{x,y,z}, R_j) - dist(T_{x,y,z}, R_k))\right]^2,$$

where $$dist(T_{x,y,z}, R_j) = \sqrt{(x_{Rj} - x)^2 + (y_{Rj} - y)^2 + (z_{Rj} - z)^2}$$

is the Euclidean distance between point (x, y, z) and the coordinates of the $j^{th}$ receiver $R_j$. The minimization solution (x', y', z') is the estimated coordinate position for the $i^{th}$ tag. In an example algorithm, this proceeds according to:

$$\varepsilon = \sum_{j=1}^{N}\left[[(x-x_j)^2 + (y-y_j)^2 + (z-z_j)^2]^{\frac{1}{2}} - c(t_j - t_0)\right]^2$$

where each arrival time, $t_j$, is referenced to a particular receiver (receiver "1") as follows:

$$t_j = \frac{1}{\beta}(N_j - N_1 - \Delta_{jk})$$

and the minimization is performed over variables (x, y, z, $t_0$) to reach a solution (x', y', z', $t_0$').

In some example embodiments, the location of a tag 102 may then be output to a receiver processing and distribution system 110 for further processing of the location data to advantageously provide visualizations, predictive analytics, statistics, and/or the like.

Figure 1B:
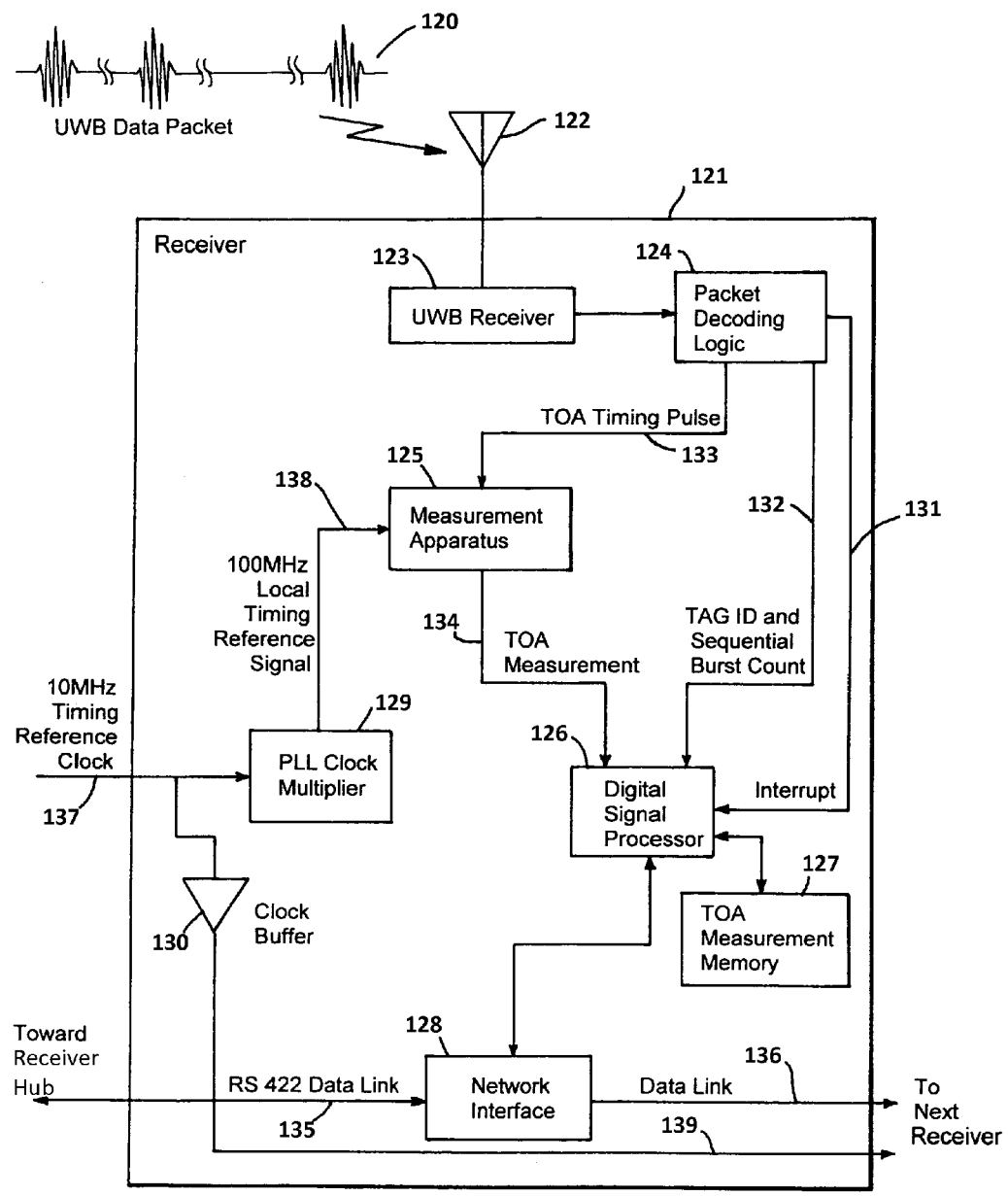
FIG. 1B illustrates an exemplary receiver in a UWB system comprising a UWB receiver that may be configured in accordance with some embodiments of the present invention.

FIG. 1B illustrates an exemplary receiver in a UWB system comprising a UWB receiver that may be configured in accordance with some embodiments of the present invention. In an example embodiment, UWB radio data packets 120 are transmitted to the receiver 121 (e.g., receiver 106 of FIG. 1) and intercepted by UWB antenna 122. A UWB receiver 123 is provided at each receiver 121. The UWB receiver can, for example, be designed in accordance with the system described in commonly-owned U.S. Pat. No. 5,901,172, which is incorporated by reference herein in its entirety.

UWB receiver 123 (e.g., receiver 106 of FIG. 1) produces a digital bit stream that is processed by packet decoding logic 124, which performs packet framing and bit timing as part of an isochronous communication system. In an isochronous system, the communication signals carry timing information embedded as part of the signal. Upon receiving a complete UWB data packet, packet decoding logic 124 generates and sends an interrupt signal on line 131 to the digital signal processor (DSP) 126. Tag ID and a sequential burst count 132 are also extracted from the packet, and are sent to the DSP 126 for further processing. Packet decoding logic 124 also generates a TOA timing pulse 133 that is precisely referenced in time relative to the beginning or end of a UWB data packet synchronization preamble. The synchronization preamble may comprise a few bits of data having a unique pattern at the beginning of the UWB packet burst so that the UWB receiver 123 may determine the validity of the received packet as well as bit time alignment. The TOA timing pulse 133 is subsequently measured by measurement apparatus 125, which functions as a time-to-digital converter. Alternatively, the TOA may be determined as an aggregate or average by measurements of the timing of a plurality of pulses. An output TOA measurement 134 is a digital result that is determined in response to receipt of the TOA timing pulse 133.

Upon receiving an interrupt signal, DSP 126 reads the TOA measurement 134 along with the optional tag ID and sequential burst count 132, and stores the combined information in the TOA measurement memory 127. Any additional information decoded by the packet decoding logic 124 (e.g., personnel data, cargo manifest, etc.) can also be stored in memory at this time. In some embodiments, the TOA measurement memory 127 operates as a First-In First-Out (FIFO) buffer. Also, in some embodiments, a program (which is typically stored in a FLASH memory, not shown) manages a portion of a general-purpose static RAM to function as the TOA measurement memory FIFO.

Because packet data and measurement results can be transferred at high speeds to TOA measurement memory 127, the receiver 121 can receive and process tag (and corresponding object) locating signals on a nearly continuous basis. That is, multiple UWB data packets 120 can be processed in close succession thereby allowing the use of hundreds to thousands of tag transmitters.

In some embodiments, data stored in TOA measurement memory 127 is sent to a receiver hub 108 (of FIG. 1) over a network interface 128 in response to a specific request from the receiver hub 108.

In addition, network interface 128 has two bi-directional data links, 135 and 136. In some embodiments, these data links may be RS422 differential serial links. The network interface 128 may receive command signals from a receiver hub 108 on link 135. For example, one such command instructs the DSP 126 to transfer the contents of the TOA measurement memory 127 to the receiver hub 108. Additional commands include those to adjust UWB receiver 123 operating characteristics such as gain and detection thresholds. The network interface 128 may also buffer the data signals between links 135 and 136. Data link 136 may then connect to the next receiver 121 (e.g., receiver 106 of FIG. 1) in a communications chain.

Within the receiver 121, a distributed timing reference clock signal on line 137 may be frequency-multiplied using well-known techniques by phased-lock loop (PLL) clock multiplier 129 thereby producing a local timing reference signal on line 138. In one embodiment, timing reference clock signal on line 137 may have a clock frequency of 10 MHz, and the local timing reference signal on line 138 may be generated at 100 MHz (i.e., a 10× digital multiplication factor), for example. An advantage of this approach is that the distributed timing reference clock signal can be made low enough in frequency so that it can be transmitted over low-cost cables (e.g., twisted pair wires). Since timing jitter of the local timing reference signal degrades as the PLL multiplier coefficient is increased, there is a necessary trade-off between frequency and jitter of the local timing reference signal and the frequency of the timing reference clock.

Utilizing a common timing reference clock, a plurality of local timing reference signals (one in each receiver) can be precisely matched in frequency. Clock buffer 130 may create a buffered copy of the timing reference clock signal at one receiver to be transmitted to the next receiver in a daisy chain fashion. Using this approach, additional receivers can be connected without concern for clock loading. Buffer delay is also not an issue since the timing reference clock is used for frequency only, and not phase, reference.

In some embodiments, clock signals 137 and 139 may be differential signals. The use of differential clock signals is advantageous since they avoid clock duty cycle distortion which can occur with the transmission of relatively high-speed clocks (e.g., >10 MHz) on long cables (e.g., >100 feet).

Example Receivers Providing Interference Rejection

Figure 2:
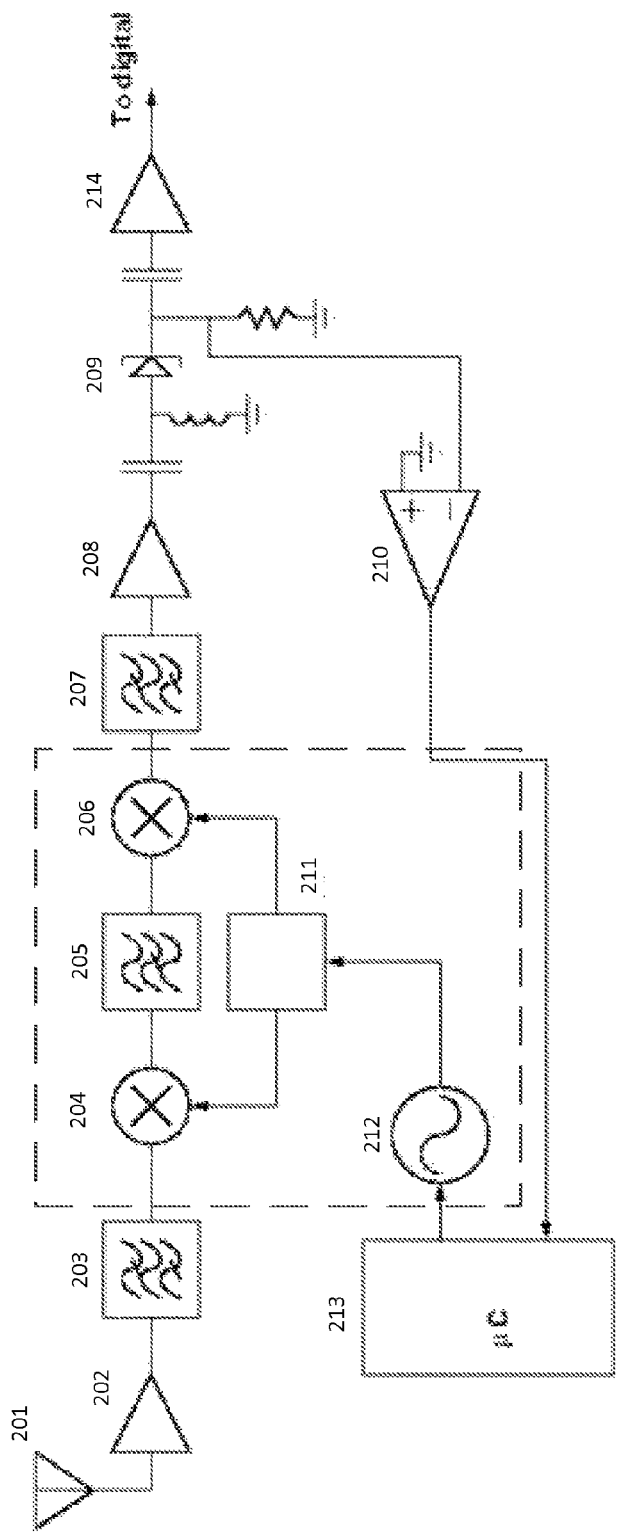
FIG. 2 illustrates a block diagram of an exemplary UWB receiver in accordance with some embodiments of the present invention.

FIG. 2 illustrates a block diagram of a first exemplary UWB receiver (e.g., receiver 106 of FIG. 1) providing interference rejection in accordance with some embodiments of the present invention. The UWB receiver of FIG. 2, which may be embodied by receiver 106, receiver 121, or the like, may comprise antenna 201, low noise amplifier (LNA) 202, bandpass filter 203, mixer 204, notch filter 205, mixer 206, bandpass filter 207, amplifier 208, detector 209, bias amplifier 210, splitter 211, voltage controlled oscillator (VCO) 212, controller 213, and baseband amplifier 214.

In this embodiment, antenna 201 may receive both the desired UWB signal and an undesired interference signal (e.g. some component of an interferer's originally transmitted signal). For example, an interferer may transmit a signal comprising a first component of the signal that may be received by antenna 201 and a second component of the signal that is directed toward the interferer's intended receiver. In some examples, the low noise amplifier (LNA) 202 may add a predetermined gain and may further improve system noise performance. The bandpass filter 203 may be configured to cover the UWB band, for example with a bandwidth of 500 MHz and a center frequency of 6.55 GHz.

The mixer 204, notch filter 205, mixer 206, splitter 211, and voltage controlled oscillator (VCO) 212 of FIG. 2 together may form a tunable notch filter. The nominal frequency of VCO 212 may be above the UWB band of interest, so as to enable mixer 204 to perform a downconversion to a lower frequency band where notch filter 205 will be easier or more cost-effective to construct for a given bandwidth and level of stop-band rejection. For example, some embodiments may use some frequency in the L-band. Mixer 206 then upconverts the notched signal, for example back into the C-band (e.g., 4.0 to 8.0 GHz) or other predetermined band, which enables bandpass filter 207, amplifier 208, detector 209, and baseband amplifier 214 to process the filtered UWB signal.

In some example embodiments, the tunable notch filter is configured to notch out (i.e., attenuate, remove, etc.) only the minimal amount of the received signal bandwidth that is necessary for interference rejection. As such, the width of notch filter 205 may be chosen to be no larger than the widest bandwidth interference signal that is expected. In typical installations of a UWB locating system, such as the locating system described with reference to FIG. 1A, the width of the notch filter need not be larger than 30 MHz at its greatest depth, corresponding to the widest bandwidth allowed for commercial services in the 5.925-7.25 GHz range by Federal Communications Commission (FCC) regulations. The amount of bandwidth that a notch filter removes from the UWB signal depends on the bandwidth of the notch filter and will necessarily be greater than the width of the notch at its greatest rejection. For example, in an exemplary 400 MHz UWB implementation, a 30 MHz notch filter with 40 dB of rejection may actually have a −3 dB bandwidth of 90 MHz, and remove 22.5% of the signal bandwidth, which will reduce the UWB signal by around 40% or approximately a 2.2 dB reduction in received signal strength. For this reason, it is desirable to use the narrowest possible notch bandwidth needed to mitigate the interference.

Detector 209 provides a DC or slowly varying output that is taken to the bias amplifier 210. Bias amplifier 210 is of a type that has a low internal offset, such that small, relatively slow, changes in the operating point of detector 209 can be measured by controller 213. Controller 213 may monitor the output of detector 209 and adjust the specific frequency of VCO 212 so as to minimize the magnitude of the slow changes in detector 209, including its DC value. For example, the controller 213 may determine whether the output of detector 209 is above a threshold level and adjust the frequency of VCO 212 based on this determination. When this detected output (e.g., the magnitude of slow changes) from detector 209 is minimal, then maximum filtering of the interference signal may be achieved.

For example, the amount that an interference signal must be suppressed is based on the signal strength of the interference signal, which in turn depends on the gain and pattern of the antenna and the direction from which the interference signals arrive. In an exemplary 400 Mhz UWB system implementation, the minimum signal strength that provides good performance may be about −70 dBm, with signal reception dropping off at about −73 dBm. To not have a significant impact on UWB performance, an interferer must be attenuated to about 15 dB below the minimum signal strength. For example, in an exemplary 400 MHz UWB system implementation, the interferer could be attenuated to −88 dBm for effective mitigation.

Figure 3:
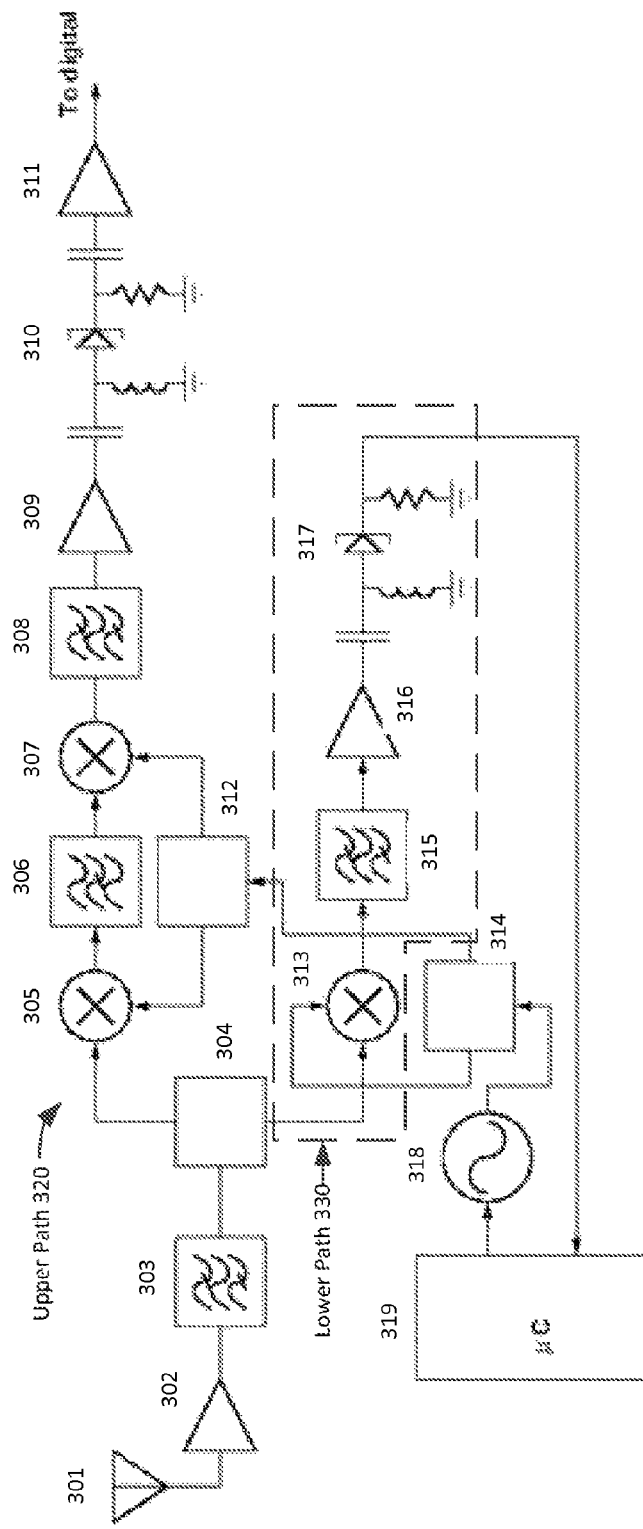
FIG. 3 illustrates a block diagram of another exemplary UWB receiver in accordance with some embodiments of the present invention.

FIG. 3 illustrates a block diagram of another exemplary UWB receiver in accordance with some embodiments of the present invention. FIG. 3 illustrates a modification to the tunable notch filter interference rejection illustrated in the UWB receiver of FIG. 2 providing an alternate-path interference detection operation. The receiver of FIG. 3, which may be embodied by receiver 106, receiver 121, or the like, may comprise antenna 301, LNA 302, bandpass filter 303, splitter 304, mixer 305, notch filter 306, mixer 307, bandpass filter 308, amplifier 309, detector 310, baseband amplifier 311, splitter 312, mixer 313, splitter 314, narrowband bandpass filter 315, amplifier 316, detector 317, VCO 318, and controller 319.

In the example embodiment of FIG. 3, antenna 301, LNA 302, and bandpass filter 303 may be configured to receive the desired UWB signal along with an interference signal (i.e., a component of an interference signal), such as was described with respect to FIG. 2. Splitter 304 then diverts this composite signal (comprising the desired UWB signal and an interference signal) into two paths, with both paths receiving the same composite signal as input.

In the upper path 320, mixer 305, notch filter 306, mixer 307, splitter 312, and VCO 318 form a tunable notch filter as described with respect to FIG. 2. Bandpass filter 308 covers the UWB band, and amplifier 309, detector 310, and baseband amplifier 311 are configured to process the filtered UWB signals.

The lower path 330, comprising mixer 313, narrowband bandpass filter 315, amplifier 316, and detector 317, forms a superheterodyne receiver tuned to the same frequency as the notch filter 306. In some examples, by tuning the superheterodyne receiver to the same frequency as the tunable notch filter 306 greater sensitivity to detection of narrowband interferers can be obtained.

Controller 319 monitors the level of interference at detector 317 and controller 319 may then adjust the specific frequency of VCO 318 to mitigate additional interference in the received signal. In one embodiment, the controller 319 determines whether the level of interference is above a threshold level and then adjusts the specific frequency of VCO 318. Splitter 314 provides the output of VCO 318 to both the tunable notch filter of the upper path 320 and to the superheterodyne receiver of the lower path 330 such that the tunable notch filter and the superheterodyne receiver are tuned to the same frequency. When the detected output from detector 317 is minimal (e.g., a minimal magnitude of slow changes at the detector), then maximum filtering of the interference signal may be achieved. An advantage of this embodiment is the increased sensitivity provided by an independent signal path with narrower bandwidth and, hence, higher allowable gain than would be possible with a shared signal path.

Figure 4:
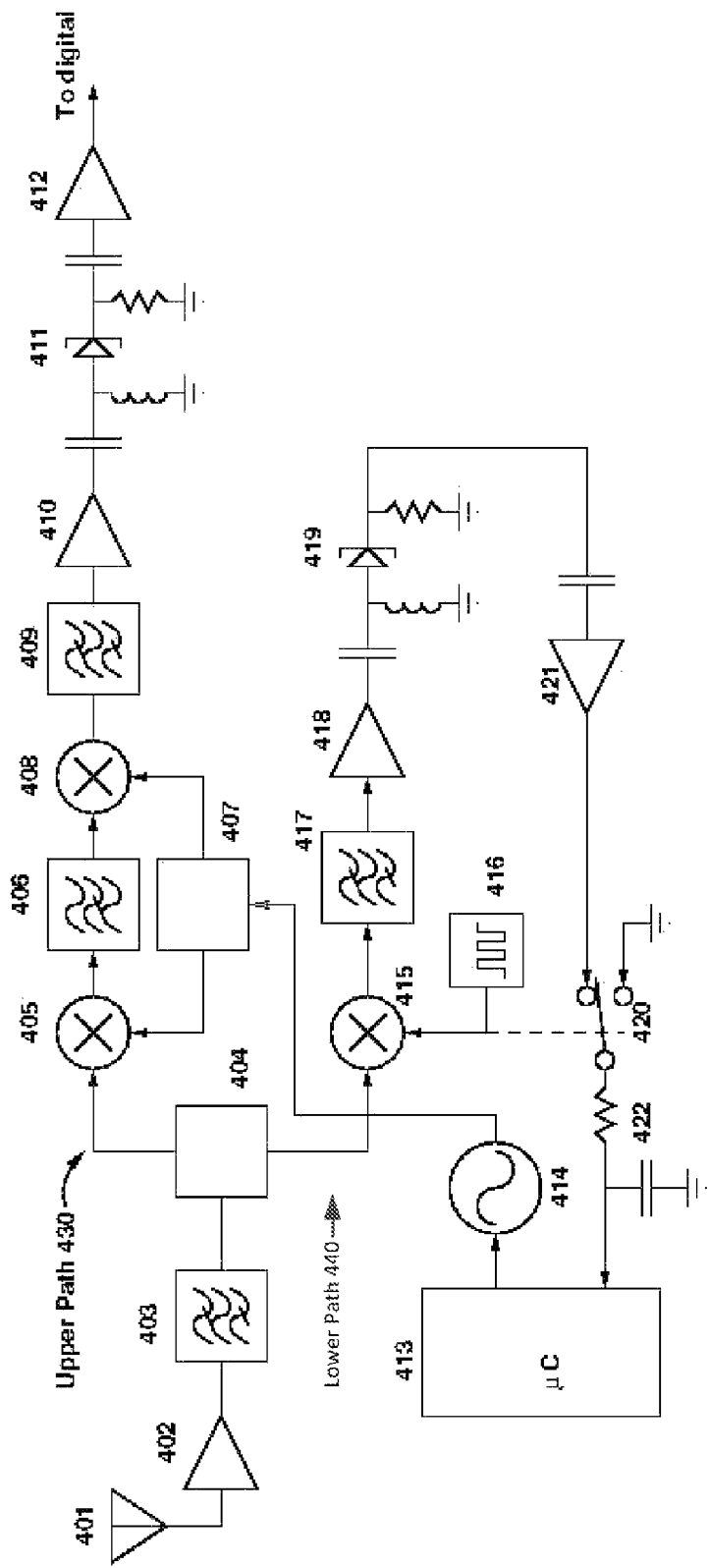
FIG. 4 illustrates a block diagram of another exemplary UWB receiver in accordance with some embodiments of the present invention.

FIG. 4 illustrates a block diagram of another exemplary UWB receiver in accordance with some embodiments of the present invention and illustrates a similar embodiment to that of FIG. 3 in which the superheterodyne receiver of the lower path 330 of FIG. 3 is replaced by a chopper-stabilized amplifier in the lower path 440 of FIG. 4. The receiver of FIG. 4, which may be embodied by receiver 106, receiver 121, or the like, may comprise antenna 401, LNA 402, bandpass filter 403, splitter 404, mixer 405, notch filter 406, splitter 407, mixer 408, bandpass filter 409, amplifier 410, detector 411, baseband amplifier 412, controller 413, VCO 414, mixer 415, squarewave source 416, bandpass filter 417, amplifier 418, detector 419, and chopper 420.

In the example embodiment of FIG. 4, antenna 401, LNA 402, and bandpass filter 403 may be configured to receive the desired UWB signal along with an interference signal (i.e., a component of an interference signal), similar to the operations described with respect to FIG. 2. In this embodiment however, splitter 404 diverts this composite signal (comprising the desired UWB signal and the interference signal) into two paths, with both paths receiving the same composite signal as input.

In the upper path 430, mixer 405, notch filter 406, mixer 408, splitter 407, and VCO 414 form a tunable notch filter as described with respect to FIG. 2. Bandpass filter 409 covers the UWB band, and amplifier 410, detector 411, and baseband amplifier 412 process the filtered UWB signals.

The lower path 440 forms a chopper-stabilized amplifier comprising mixer 415, square wave source 416, bandpass filter 417, amplifier 418, detector 419, AC coupled amplifier 421, chopper 420, and low-pass filter 422. In this approach, bandpass filter 417 can accept the entire UWB band, while good sensitivity of the interference signal can be obtained without being affected by DC offset shifts in the various components, due to AC coupling throughout.

Controller 413 monitors the level of interference at detector 419 and controller 413 may then adjust the specific frequency of VCO 414 to mitigate additional interference in the received signal. In one embodiment, the controller 413 determines whether the level of interference is above a threshold level and then adjusts the specific frequency of VCO 414. When the detected output from detector 419 is minimal, then maximum rejection of the interference signal may be achieved.

Figure 5:
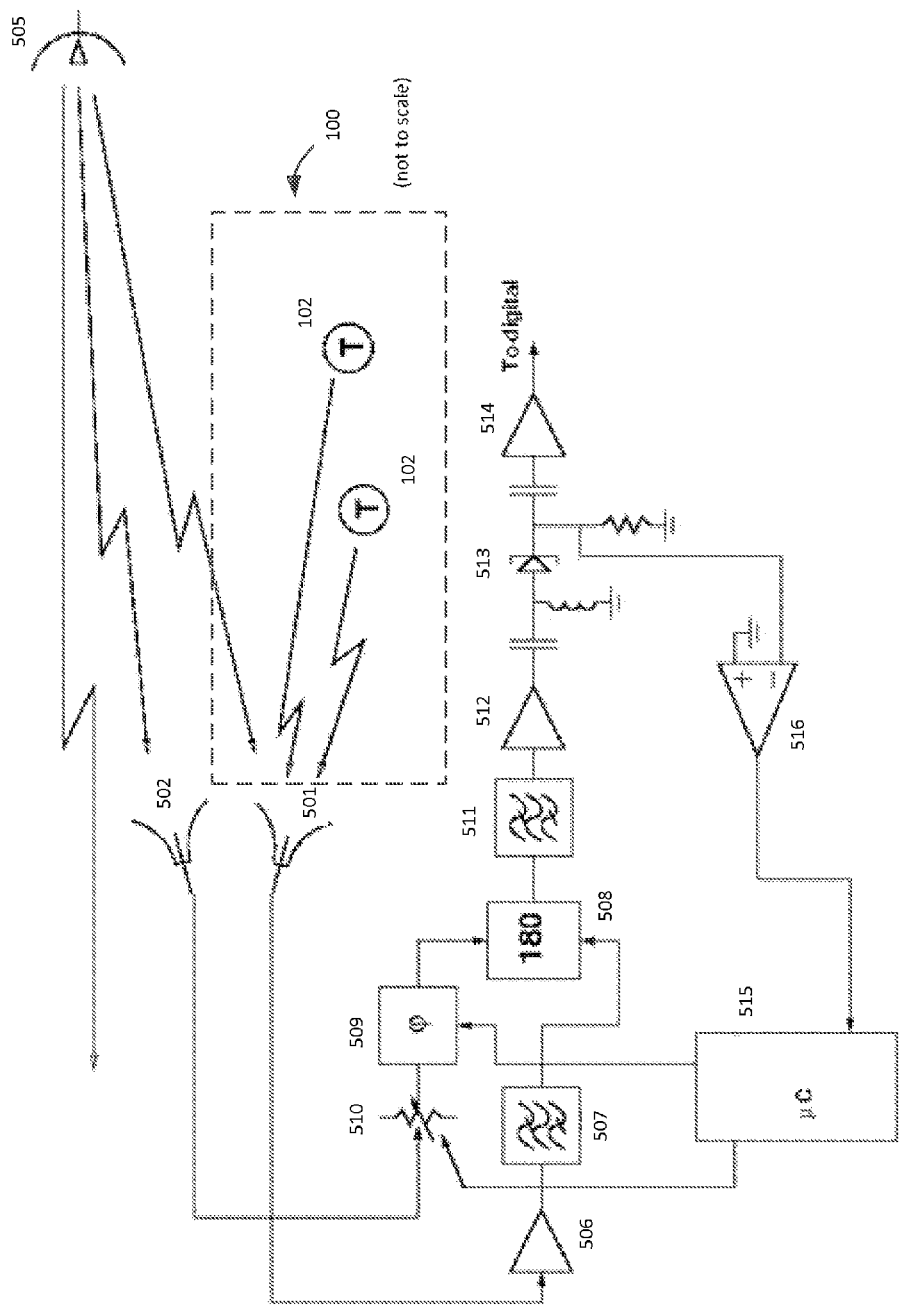
FIG. 5 illustrates a block diagram of another exemplary UWB receiver in accordance with some embodiments of the present invention.

FIG. 5 illustrates a block diagram of another exemplary UWB receiver in accordance with some embodiments of the present invention. FIG. 5 illustrates an example embodiment of a receiver, which may be configured to use directional receive antennas to focus the system reception area on a particular region so as to mitigate interference that may originate outside that particular region.

For example, in an open air stadium such as the football stadium of FIG. 1A, a plurality of tags 102 may be attached to objects (i.e., football players, the football, field markers, etc.). Such tags 102 would thus move about the monitored region (i.e., the playing field) while broadcasting their respective signals. An interference source (not shown in FIG. 1A) such as a telecommunications tower positioned outside the stadium may broadcast interference signals proximate to or through the monitored region.

Returning to FIG. 5, the interference source 505 may transmit focused beams that substantially bypass the stadium except for stray signals (or components thereof) that are refracted into the stadium and thus interfere with the UWB system coverage area of the monitored region. In this example embodiment, the receiver may comprise a directional receive antenna 501 that can be used to detect one or more tags 102 on the field of the stadium (e.g., monitored region 100). The directional receive antenna 501 may have a beam pattern which is substantially more directed toward the desired tag signals (e.g., UWB system coverage region or monitored region 100) and less directed toward the stray signals from interference source 505.

A second sampling antenna 502 can be oriented or otherwise directed away from the UWB system coverage region (e.g., desired tags 102/monitored region 100), and oriented or otherwise directed more toward interference source 505. In some embodiments, the two signal paths (from antenna 501 and antenna 502) can be combined in such a way as to reduce the undesired effects of the interference source 505.

The example receiver of FIG. 5 may comprise directional receive antenna 501, sampling antenna 502, LNA 506, bandpass filter 507, combiner 508, variable phase shifter 509, variable attenuator 510, bandpass filter 511, amplifier 512, detector 513, baseband amplifier 514, controller 515, and bias amplifier 516.

In the example receiver of FIG. 5, the desired UWB signals, along with a first component of an interference signal, may be received by directional receive antenna 501, LNA 506, and bandpass filter 507, similarly to the operation described with respect to FIG. 2. The composite signal (comprising the desired UWB signal and the first component of the interference signal) then passes through combiner 508 and onto the remaining stages of a conventional UWB receiver (e.g., receiver 106), comprising bandpass filter 511, RF amplifier 512, detector 513, and baseband amplifier 514, similarly to the operations described with respect to FIG. 2.

Sampling antenna 502 may also receive a signal comprising the second component of the interference signal and the UWB signal but in different proportion than the receive antenna 501. The sampling antenna 502 may receive a signal in which the ratio of the signal strength of the interference signal to that of the UWB signal is substantially greater than the corresponding ratio for the receive antenna 501. The presence of combiner 508 allows a signal from sampling antenna 502 to be summed in opposition to the composite signal from directional receive antenna 501. Since the ratio of signal strengths of the interference and UWB signals differ in the two paths from antennas 501 and 502, a combination of the two signal paths is enabled which provides substantially more cancellation to the interference signal than to the UWB signal at the output of combiner 508.

Variable attenuator 510 and variable phase shifter 509 are under control of controller 515 which, as before, monitors the level of interference at detector 513 passed through bias amplifier 516. Adjustments, in some example embodiments, may then be made by controller 515 (e.g., when the interference level is above a threshold level) so as to minimize the DC or slowly varying components of the signal at detector 513 so as to mitigate the interference.

Additionally or alternatively, in some embodiments, the receiver of FIG. 5 may also be modified to use alternate-path interference detection schemes such as described with respect to FIGS. 3 and 4.

Figure 6:
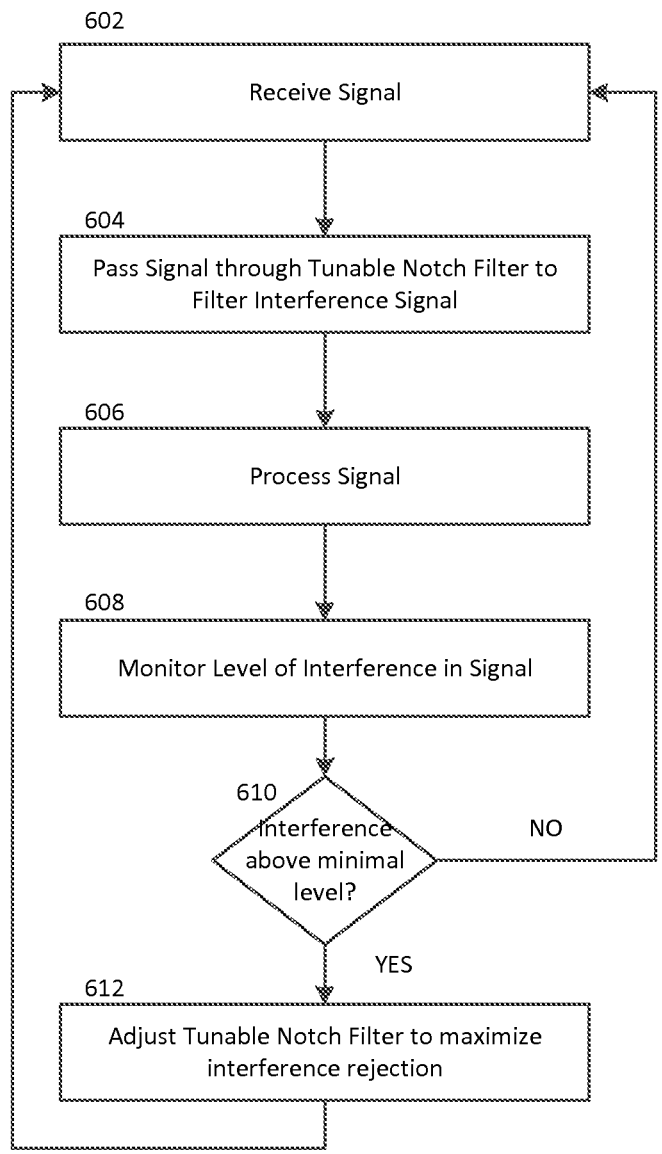
FIG. 6 illustrates a flowchart of an example process that may be used in providing interference rejection in accordance with some embodiments of the present invention.

FIG. 6 illustrates a flowchart of an exemplary process for interference rejection in a UWB location system in accordance with some embodiments of the present invention. The process may start at 602, where the receiver antenna receives a composite signal containing both the desired UWB signal and components of an interference signal. The composite signal may be passed through a LNA and bandpass filter to a tunable notch filter which may comprise a first mixer, a notch filter, a second mixer, a splitter, and a VCO, such as illustrated in FIGS. 2 through 4.

At 604, the composite signal may be passed through the tunable notch filter to filter out an amount of the received signal bandwidth (e.g., attenuate a particular frequency band) to provide rejection of the interference signal. The filtered signal may then pass through a bandpass filter, amplifier, detector, and baseband amplifier for processing of the filtered UWB signal at 606.

At 608, a controller monitors the level of interference at the detector, such as by monitoring the DC or slowly varying components of the signal at the detector, as described in regard to FIGS. 2 through 4 above. At 610, the controller may determine whether the signal, monitored at the detector, contains more than a threshold amount of interference. If so, the controller may adjust the specific frequency of the VCO to adjust the tunable notch filter and improve the interference filtering at 612. Operation may then return to 602 to continue receiving the composite signal.

Figure 7:
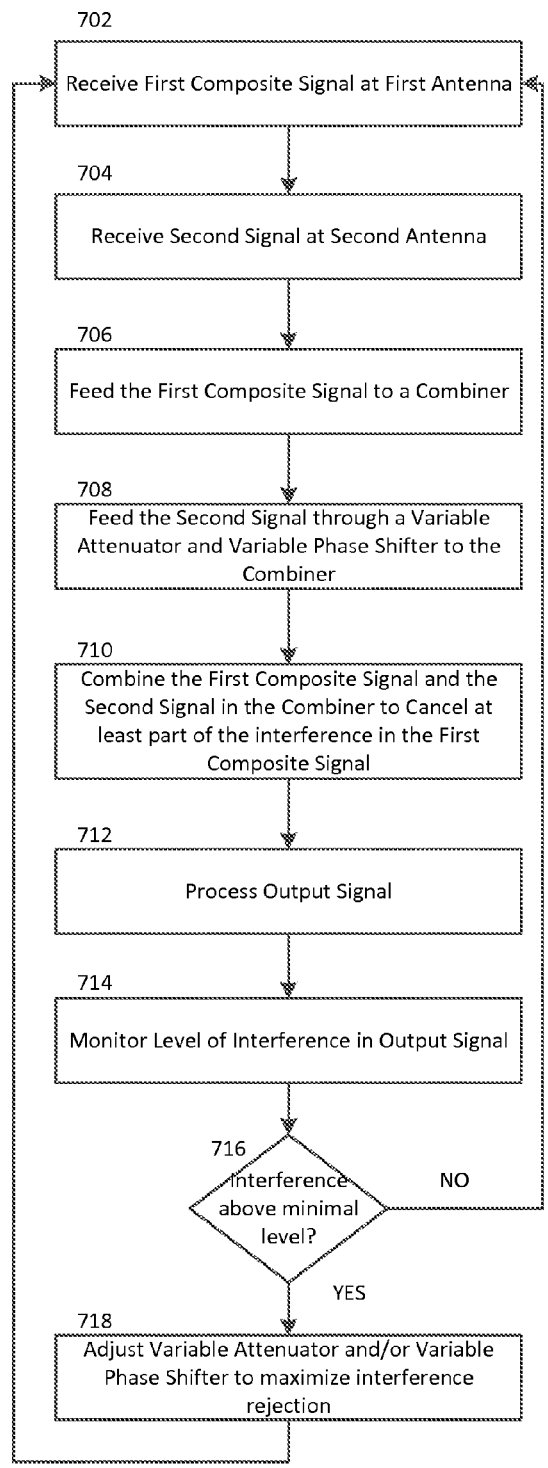
FIG. 7 illustrates a flowchart of an example process that may be used in providing interference rejection in accordance with some embodiments of the present invention.

FIG. 7 illustrates a flowchart of another exemplary process for interference rejection in a UWB location system in accordance with some embodiments of the present invention. The process may start at 702, where a first antenna (e.g., directional receive antenna 501 of FIG. 5) may receive a first composite signal containing both the desired UWB signal and first component of an interference signal. At 704, a second antenna (e.g., sampling antenna 501 of FIG. 5) may receive a second signal (e.g., comprising a higher signal strength second component of the interference signal). At 706, the first composite signal may be passed through a LNA and bandpass filter to a combiner (e.g., combiner 508 of FIG. 5). At 708, the second signal may also be passed to the combiner, such as through a variable attenuator and a variable phase shifter as illustrated in FIG. 5.

At 710, the first composite signal and the second signal may be combined in such a way as to reduce the effects of the interference signal in the output signal. For example, the combiner may sum the second signal in opposition to the first composite signal to provide a combination signal which provides substantially more cancellation to the interference signal than to the UWB signal. The combined (or output) signal may then pass through a bandpass filter, amplifier, detector, and baseband amplifier for processing of the filtered UWB signal at 712.

At 714, the controller may monitor the level of interference at the detector, such as by monitoring the DC or slowly varying components of the signal at the detector, as described with respect to FIG. 5 above. At 716, the controller may determine whether the signal monitored at the detector contains more than a threshold amount of interference. If so, at 718, the controller may adjust the variable attenuator and/or the variable phase shifter to modify the second signal before it is input to the combiner so as to improve the interference filtering. Operation may then return to 702 to continue receiving the first composite signal.

In some embodiments, certain ones of the operations above may be modified or further amplified as described below. Moreover, in some embodiments additional optional operations may also be included. It should be appreciated that each of the modifications, optional additions or amplifications below may be included with the operations above either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An ultra-wideband (UWB) receiver comprising:
an antenna configured to receive a composite signal, the composite signal comprising a UWB signal and an interference signal;
a tunable notch filter comprising a first mixer, a notch filter, a second mixer, a splitter, and a voltage controlled oscillator, the tunable notch filter configured to attenuate a part of the composite signal representing the interference signal thereby generating a filtered signal;
a detector configured to receive the filtered signal from the tunable notch filter;
a bias amplifier configured to:
receive an output of the detector; and
indicate changes in an operating point of the detector based on the output; and
a controller configured to:
monitor the changes indicated by the bias amplifier to determine an interference level associated with the filtered signal; and
adjust the tunable notch filter to reduce the interference level in an instance in which the interference level is above a threshold level.

2. The UWB receiver of claim 1 wherein the controller is configured to adjust a frequency of the voltage controlled oscillator in an instance in which the interference level is above the threshold level.

3. The UWB receiver of claim 2 wherein the voltage controlled oscillator is configured to tune the tunable notch filter.

4. The UWB receiver of claim 1, wherein the first mixer is configured to perform a downconversion of the received composite signal; the notch filter is configured to attenuate the part of the composite signal representing the interference signal; the second mixer is configured to upconvert a filtered signal back to the desired band; the splitter is configured to provide an output of the voltage controlled oscillator to the first mixer and the second mixer; and the voltage controlled oscillator is configured to tune the tunable notch filter.

5. The UWB receiver of claim 1 wherein the detector is comprised within an analog portion of the UWB receiver.

6. A method for providing interference rejection, the method comprising:
receiving a composite signal, the composite signal comprising a ultra-wideband (UWB) signal transmitted from within a monitored region and an interference signal transmitted from a source positioned outside the monitored region;
filtering at least a first component of the composite signal representing the interference signal using a tunable notch filter to generate a filtered signal, the tunable notch filter comprising a first mixer, a notch filter, a second mixer, a splitter, and a voltage controlled oscillator;
providing the filtered signal to a detector;
determining, via a bias amplifier, changes in an operating point of the detector;
monitoring, via a processor, the changes indicated by the bias amplifier to determine an interference level in the filtered signal; and adjusting, via the processor, the tunable notch filter to reduce the interference level in an instance in which the determined interference level is above a threshold level.

7. The method of claim 6 wherein the filtering of the composite signal comprises attenuating the interference level of the composite signal using the tunable notch filter, a width of the tunable notch filter corresponding to the widest bandwidth allowed for commercial services in the 5.925-7.25 GHz range.

8. The method of claim 6, wherein adjusting the tunable notch filter comprises adjusting a frequency of the voltage controlled oscillator in an instance in which the determined interference level is above the threshold level.

9. The method of claim 6 wherein adjusting the tunable notch filter comprises adjusting the variable controlled oscillator to tune the tunable notch filter.

10. The method of claim 6 wherein the composite signal is received by an ultra-wideband (UWB) receiver.

11. The method of claim 6, further comprising:
downconverting, via the first mixer, the received composite signal;
attenuating, via the notch filter, the part of the composite signal representing the interference signal;
upconverting, via the second mixer, the filtered signal back to a desired band;
providing, via the splitter, an output of the voltage controlled oscillator to the first mixer and the second mixer; and
tuning, via the voltage controlled oscillator, the tunable notch filter.

12. An apparatus for providing interference rejection, the apparatus comprising a processor and a memory including computer program code, the memory and the computer program code configured to, with the processor, cause the apparatus at least to:
receive a composite signal, the composite signal comprising a ultra-wideband (UWB) signal transmitted from within a monitored region and an interference signal transmitted from a source positioned outside the monitored region;
filter at least a first component of the composite signal representing the interference signal using a tunable notch filter to generate a filtered signal, the tunable notch filter comprising a first mixer, a notch filter, a second mixer, a splitter, and a voltage controlled oscillator;
provide the filtered signal to a detector;
determine, via a bias amplifier, changes in an operating point of the detector;
monitor the changes determined by the bias amplifier to determine an interference level in the filtered signal; and
adjust the tunable notch filter to reduce the interference level in an instance in which the determined interference level is above a threshold level.

13. The apparatus of claim 12 wherein the memory and the computer program code are further configured to, with the processor, cause the apparatus to filter at least the first component by attenuating the interference level of the composite signal using the tunable notch filter, a width of the tunable notch filter corresponding to the widest bandwidth allowed for commercial services in the 5.925-7.25 GHz range.

14. The apparatus of claim 12, wherein the memory and the computer program code are further configured to, with the processor, cause the apparatus to adjust a frequency of the voltage controlled oscillator in an instance in which the determined interference level is above the threshold level.

15. The apparatus of claim 12 wherein the memory and the computer program code are further configured to, with the processor, cause the apparatus to adjust the variable controlled oscillator to tune the tunable notch filter.

16. The apparatus of claim 12 wherein the composite signal is received by an ultra-wideband (UWB) receiver.

17. The apparatus of claim 12, wherein the first mixer is configured to perform a downconversion of the received composite signal, the notch filter is configured to attenuate the part of the composite signal representing the interference signal, the second mixer is configured to upconvert a filtered signal back to the desired band, the splitter is configured to provide an output of the voltage controlled oscillator to the first mixer and the second mixer; and the voltage controlled oscillator is configured to tune the tunable notch filter.

* * * * *